United States Patent
Calderon et al.

(10) Patent No.: US 10,966,601 B2
(45) Date of Patent: Apr. 6, 2021

(54) VAGINAL SPECULUM WITH ELECTROMYOGRAPHIC SENSORS

(71) Applicants: Ilan Calderon, Bet Lechem Haglilit (IL); Gal Ben-David, Adi (IL)

(72) Inventors: Ilan Calderon, Bet Lechem Haglilit (IL); Gal Ben-David, Adi (IL)

(73) Assignee: OB Tools Ltd., Nesher (IL)

( * ) Notice: Subject to any disclaimer, the term of this patent is extended or adjusted under 35 U.S.C. 154(b) by 149 days.

(21) Appl. No.: 14/722,284

(22) Filed: May 27, 2015

(65) Prior Publication Data

US 2016/0345817 A1    Dec. 1, 2016

(51) Int. Cl.

| | |
|---|---|
| *A61B 1/32* | (2006.01) |
| *A61B 5/04* | (2006.01) |
| *A61B 17/435* | (2006.01) |
| *A61B 5/03* | (2006.01) |
| *A61B 1/303* | (2006.01) |
| *A61B 5/0488* | (2006.01) |
| A61B 5/0492 | (2006.01) |
| A61B 5/00 | (2006.01) |

(52) U.S. Cl.
CPC ............... *A61B 1/32* (2013.01); *A61B 1/303* (2013.01); *A61B 5/04882* (2013.01); *A61B 17/435* (2013.01); *A61B 5/033* (2013.01); *A61B 5/04012* (2013.01); *A61B 5/0492* (2013.01); *A61B 5/435* (2013.01); *A61B 5/4848* (2013.01); *A61B 5/7246* (2013.01); *A61B 2560/0468* (2013.01)

(58) Field of Classification Search
None
See application file for complete search history.

(56) References Cited

U.S. PATENT DOCUMENTS

| | | | | |
|---|---|---|---|---|
| 1,950,788 | A | * | 3/1934 | Ewerhardt ............... A61N 1/06 607/138 |
| 3,933,147 | A | * | 1/1976 | Du Vall ............... A61N 1/0512 600/591 |
| 4,396,019 | A | * | 8/1983 | Perry, Jr. ................ A61B 5/042 600/546 |
| 4,577,640 | A | * | 3/1986 | Hofmeister .......... A61B 5/0422 600/551 |

(Continued)

FOREIGN PATENT DOCUMENTS

| | | |
|---|---|---|
| CN | 201094620 | 8/2008 |
| CN | 103179899 | 6/2013 |

(Continued)

OTHER PUBLICATIONS

PCT Search Report and Written Opinion PCT/IB2016/053068, dated Sep. 20, 2016.

(Continued)

*Primary Examiner* — Charles A Marmor, II
*Assistant Examiner* — Benjamin S Melhus
(74) *Attorney, Agent, or Firm* — Dekel Patent Ltd.; David Klein

(57) ABSTRACT

A vaginal speculum includes a spreading element and at least two electromyographic sensors. At least one of the electromyographic sensors is mounted in or on the spreading element. The electromyographic sensors generate signals indicative of electromyographic activity in a vagina, cervix, or uterus.

1 Claim, 1 Drawing Sheet

(56) References Cited

U.S. PATENT DOCUMENTS

| | | | | |
|---|---|---|---|---|
| 4,827,946 A * | 5/1989 | Kaali | A61F 6/08 128/830 |
| 4,934,378 A * | 6/1990 | Perry, Jr. | A61B 5/486 600/546 |
| 4,971,036 A * | 11/1990 | Collins | A61B 1/32 600/202 |
| 5,010,895 A * | 4/1991 | Maurer | A61B 1/32 607/138 |
| 5,154,177 A * | 10/1992 | Eisman | A61B 5/0492 600/373 |
| 5,259,388 A * | 11/1993 | Eisman | A61N 1/0512 600/546 |
| 5,373,852 A * | 12/1994 | Harrison | A61B 5/0002 128/903 |
| 5,411,548 A * | 5/1995 | Carman | A61B 5/04882 607/138 |
| 5,546,953 A * | 8/1996 | Garfield | A61B 5/04882 600/546 |
| 5,623,939 A * | 4/1997 | Garfield | A61B 5/04882 600/546 |
| 5,662,699 A * | 9/1997 | Hamedi | A61N 1/0524 607/138 |
| 5,776,073 A * | 7/1998 | Garfield | A61B 5/04882 600/546 |
| 5,800,501 A * | 9/1998 | Sherlock | A61N 1/0524 600/373 |
| 6,468,232 B1 * | 10/2002 | Ashton-Miller | A61B 5/227 600/591 |
| 6,480,746 B1 * | 11/2002 | Ingle | A61B 18/1485 128/898 |
| 6,694,192 B2 * | 2/2004 | Policker | A61N 1/36007 600/304 |
| 6,741,895 B1 * | 5/2004 | Gafni | A61B 5/4337 600/38 |
| 6,905,471 B2 * | 6/2005 | Leivseth | A63B 23/20 600/591 |
| 7,447,542 B2 * | 11/2008 | Calderon | A61B 5/04882 600/546 |
| 8,060,195 B2 * | 11/2011 | Gurewitsch | A61B 5/4331 600/547 |
| 8,192,357 B2 | 6/2012 | Miles | |
| 8,439,845 B2 * | 5/2013 | Folkerts | A61B 5/0048 600/557 |
| 8,444,571 B2 * | 5/2013 | Folkerts | A61B 5/1107 600/557 |
| 8,972,028 B2 * | 3/2015 | Garfield | A61N 1/0521 607/138 |
| 8,983,627 B2 * | 3/2015 | Pelger | A63B 23/20 607/138 |
| 9,622,732 B2 * | 4/2017 | Martinelli | A61B 17/0218 |
| 10,052,477 B2 * | 8/2018 | Bozzarelli | A61N 1/0524 |
| 2002/0010494 A1 * | 1/2002 | Policker | A61N 1/36007 607/41 |
| 2002/0193670 A1 * | 12/2002 | Garfield | A61B 5/0444 600/304 |
| 2005/0010127 A1 | 1/2005 | Calderon | |
| 2006/0036188 A1 * | 2/2006 | Hoffman | A61B 5/0002 600/591 |
| 2007/0043264 A1 * | 2/2007 | Gillis | A61B 1/303 600/184 |
| 2008/0167553 A1 * | 7/2008 | Paltieli | A61B 8/0866 600/437 |
| 2009/0143649 A1 * | 6/2009 | Rossi | A61B 1/32 600/221 |
| 2010/0305406 A1 * | 12/2010 | Braun | H01C 17/12 600/202 |
| 2011/0105850 A1 * | 5/2011 | Voegele | A61B 17/3423 600/207 |
| 2011/0202108 A1 * | 8/2011 | Gross | A61N 1/36007 607/46 |
| 2012/0197112 A1 * | 8/2012 | McNichols | A61B 5/066 600/425 |
| 2013/0053863 A1 * | 2/2013 | Juravic | A61M 29/02 606/119 |
| 2014/0012190 A1 * | 1/2014 | Ben-David | A61N 1/36014 604/66 |
| 2014/0235950 A1 * | 8/2014 | Miles | A61B 5/0492 600/202 |

FOREIGN PATENT DOCUMENTS

| | | |
|---|---|---|
| EP | 2689724 | 1/2014 |
| WO | 2012/021976 | 2/2012 |

OTHER PUBLICATIONS

Melamie Morin et al., "Application of a new method in the study of pelvic floor muscle passive properties in continent women", Journal of Electromyography and Kinesiology, vol. 20, No. 5, Oct. 1, 2010, pp. 795-803.

* cited by examiner

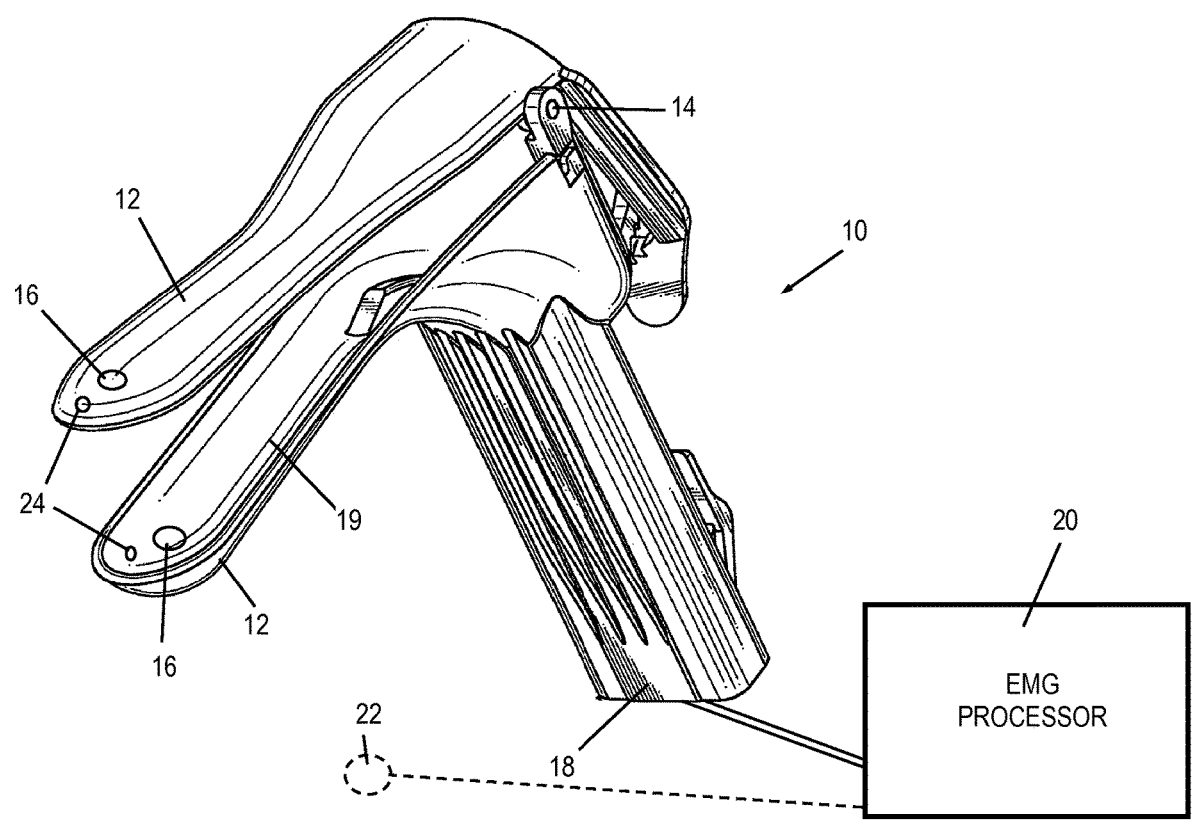

US 10,966,601 B2

VAGINAL SPECULUM WITH ELECTROMYOGRAPHIC SENSORS

FIELD OF THE INVENTION

The present invention generally relates to vaginal specula, and more specifically to a vaginal speculum with electromyographic sensors.

BACKGROUND OF THE INVENTION

As is well known in the art, a vaginal speculum has two "duck-bill" spreading members which are pivotally interconnected. The vaginal speculum is typically used to dilate the vaginal cavity so that an examination or treatment of the cervix and vaginal tissues may be readily performed.

SUMMARY OF THE INVENTION

The present invention seeks to provide a novel vaginal speculum with electromyographic sensors, as is described in detail further hereinbelow. The invention may be used for direct measurement of the electromyographic activity in the vagina, cervix, or uterus.

The system of the invention has many applications, such as without limitation, determination of a characteristic of uterine contractions, determination of intra-uterine pressure correlated to electromyographic activity, treatment of menstrual-related pain for non-pregnant women, measurement of electromyographic activity in the uterus for IVF reintroduction of fertilized eggs when the uterus is non-active to prevent rejection of fetuses, or monitoring pregnant women during or before birth, such as direct and more accurate measurement of electromyographic activity in the uterus, sensing fetal heartbeat, measurement of efficacy of drugs for increasing or decreasing contractions or for accelerating or decelerating uterine activity.

There is thus provided in accordance with an embodiment of the present invention a vaginal speculum including a spreading element and at least two electromyographic sensors, at least one of the electromyographic sensors being mounted in or on the spreading element, the electromyographic sensors operative to generate signals indicative of electromyographic activity in a vagina, cervix, or uterus.

In accordance with an embodiment of the present invention the electromyographic sensors are in electrical communication with an electromyographic processor.

In accordance with an embodiment of the present invention the spreading element includes more than one spreading element each of which has mounted therein or thereon at least one of the electromyographic sensors.

In accordance with an embodiment of the present invention the spreading element includes more than one spreading element each of which has mounted therein or thereon at least two of the electromyographic sensors.

In accordance with an embodiment of the present invention at least one of the electromyographic sensors includes a surface electromyographic sensor.

In accordance with an embodiment of the present invention at least one of the electromyographic sensors includes an intramuscular electromyographic sensor.

In accordance with an embodiment of the present invention a position sensor may be mounted in or on the speculum.

BRIEF DESCRIPTION OF THE DRAWINGS

The present invention will be understood and appreciated more fully from the following detailed description taken in conjunction with the drawing in which:

FIG. 1 is a simplified illustration of a vaginal speculum with electromyographic sensors, constructed and operative in accordance with a non-limiting embodiment of the present invention.

DETAILED DESCRIPTION OF EMBODIMENTS

Reference is now made to FIG. 1, which illustrates a vaginal speculum 10 in accordance with a non-limiting embodiment of the present invention.

Speculum 10 may include one or more spreading elements 12, such as blades 12, which may be pivotally interconnected at a pivot 14. However, the invention is not limited to the particular construction of the spreading elements or any adjustment devices used in the speculum; rather the invention is applicable for any type of vaginal speculum.

Speculum 10 includes one or more electromyographic sensors 16, which may be mounted in or on any of the spreading elements 12. In one embodiment, electromyographic (EMG) sensors 16 are surface EMG sensors, such as a pair of Ag/AgCl electrodes mounted at distal portions of spreading elements 12, or alternatively at other portions of the spreading elements 12. (Optional reference electrode(s) may also be used.) The spreading elements 12 come into direct contact with the vaginal, cervical or uterine wall. The signals from the surface EMG sensors 16 are sent to an electrical connector 18 (such as via wired connection 19 or wireless connection, e.g., Bluetooth) which is in electrical communication with an EMG monitor or processor 20, such as the EUM-100 Pro system, commercially available from OB Tools Ltd., Israel. The EMG monitor can determine the presence, effectiveness, frequency and intensity of uterine contractions. The EMG sensors 16 serve as uterine electrical activity sensors. The combination of the speculum 10, EMG sensors 16 and EMG processor 20 forms a system for direct measurement of the electromyographic activity in the vagina, cervix, or uterus. The information from the EMG sensors can be used to determine other phenomena, such as but not limited to, intra-uterine pressure which is correlated to the electromyographic activity.

In the illustrated embodiment, there is a pair of EMG sensors 16 disposed in or on each spreading element 12. The use of more than one EMG sensor on each spreading element 12 helps reduce noise in the signals from the sensors. Alternatively, only one sensor 16 may be used in the speculum 10 which cooperates with an external sensor or electrode 22 (shown in broken lines in FIG. 1). The external electrode may be used as a reference electrode.

As is known in the art, surface EMG sensors sense muscle activity on the skin surface above the muscle by sensing the voltage difference between two separate electrodes, or between each electrode and the reference electrode. The sensed data is that of superficial muscle activity to a limited depth.

In another embodiment, EMG sensors 16 are intramuscular EMG sensors. For example, a single EMG sensor 16 may be provided on speculum 10, in which the sensor is a monopolar needle electrode, which cooperates with a surface electrode as a reference. More than one needle electrode may be employed and the system may operate in monopolar, bipolar or combined monopolar/bipolar modes of operation. The needle electrode pierces the skin of the patient and measures the electromyographic activity in the vagina, cervix, or uterus.

In another embodiment, speculum 10 may also include one or more position sensors 24, as described in U.S. Pat.

No. 7,447,542 to Calderon et al. The processor 20 processes data of the EMG system and the three-dimensional position information from the position sensors to provide an output of electromyographic activity data in three-dimensional space.

What is claimed is:

1. A method comprising:

introducing a vaginal speculum into a vagina, said vaginal speculum comprising a spreading element and at least two electromyographic sensors, at least one of said electromyographic sensors being mounted in or on said spreading element, and using said electromyographic sensors to measure electromyographic activity in the uterus for IVF re-introduction of fertilized eggs when the uterus is non-active to prevent rejection of fetuses; and using the electromyographic activity measured by said electromyographic sensors to detect when the uterus is non-active, and when the uterus is non-active, further comprising re-introducing fertilized eggs into the uterus.

* * * * *